US011846693B2

(12) United States Patent
Shibuya et al.

(10) Patent No.: US 11,846,693 B2
(45) Date of Patent: Dec. 19, 2023

(54) MAGNETIC FIELD CALIBRATION DEVICE AND METHOD OF CALIBRATING MAGNETISM MEASUREMENT DEVICE USING THE SAME

(71) Applicants: TDK Corporation, Tokyo (JP); Kanazawa Institute of Technology, Ishikawa (JP)

(72) Inventors: Tomohiko Shibuya, Tokyo (JP); Yoshiaki Adachi, Ishikawa (JP)

(73) Assignees: TDK Corporation, Tokyo (JP); Kanazawa Institute of Technology, Ishikawa (JP)

(*) Notice: Subject to any disclaimer, the term of this patent is extended or adjusted under 35 U.S.C. 154(b) by 255 days.

(21) Appl. No.: 17/413,887

(22) PCT Filed: Jan. 9, 2020

(86) PCT No.: PCT/JP2020/000444
§ 371 (c)(1),
(2) Date: Jun. 14, 2021

(87) PCT Pub. No.: WO2020/145344
PCT Pub. Date: Jul. 16, 2020

(65) Prior Publication Data
US 2022/0057470 A1    Feb. 24, 2022

(30) Foreign Application Priority Data

Jan. 11, 2019  (JP) .................................. 2019-003753

(51) Int. Cl.
*G01R 35/00* (2006.01)
*G01R 33/09* (2006.01)

(52) U.S. Cl.
CPC ......... *G01R 35/007* (2013.01); *G01R 33/093* (2013.01); *G01R 33/096* (2013.01); *G01R 33/098* (2013.01)

(58) Field of Classification Search
CPC ... G01R 35/007; G01R 33/093; G01R 33/096
See application file for complete search history.

(56) References Cited

U.S. PATENT DOCUMENTS

2015/0145625 A1    5/2015  Fukasawa et al.
2018/0017634 A1*   1/2018  Ueda ................. G01R 33/091
(Continued)

FOREIGN PATENT DOCUMENTS

JP    2015-102512 A    6/2015
JP    2018-072332 A    5/2018
WO    2018/058063 A1   3/2018

OTHER PUBLICATIONS

Y. Adachi et al., "Calibration for a Multichannel Magnetic Sensor Array of a Magnetospinography System", IEEE Transactions On Magnetics, vol. 50, No. 11, Nov. 2014.
(Continued)

*Primary Examiner* — Alvaro E Fortich
(74) *Attorney, Agent, or Firm* — Rimon P.C.; Tomoki Tanida

(57) ABSTRACT

A magnetic field calibration device is used to calibrate a magnetism measurement device having a plurality of magnetic sensors and includes a first holder having a first holding surface, a second holder having a second holding surface having a fixed relative positional relation with the first holding surface, and magnetism generating parts fixed to the first holding surface and the second holding surface. Thus, calibration can be completed with a single operation by assigning the first and second holding surfaces of the magnetic field calibration device respectively to the first and second measurement surfaces of the magnetism measure- (Continued)

ment device. In addition, since the relative positional relation between the first and second holding surfaces is fixed, measurement results obtained from the individual measurement surfaces match each other.

18 Claims, 10 Drawing Sheets

(56) References Cited

U.S. PATENT DOCUMENTS

| | | | | |
|---|---|---|---|---|
| 2018/0120406 A1* | 5/2018 | Blagojevic | ......... | G01R 33/0017 |
| 2019/0298202 A1* | 10/2019 | Nakamura | ......... | G01R 33/0206 |
| 2019/0377035 A1* | 12/2019 | Nakamura | ......... | G01R 33/0011 |

OTHER PUBLICATIONS

International Search Report issued in corresponding Internation Patent Application No. PCT/JP2020/000444, dated Mar. 24, 202, with English translation.

* cited by examiner

MAGNETIC FIELD CALIBRATION DEVICE AND METHOD OF CALIBRATING MAGNETISM MEASUREMENT DEVICE USING THE SAME

CROSS REFERENCE

This application is the U.S. National Phase under 35 U.S.C. § 371 of International Application No. PCT/JP2020/000444, filed on Jan. 9, 2020, which claims the benefit of Japanese Application No. 2019-003753, filed on Jan. 11, 2019, the entire contents of each are hereby incorporated by reference.

TECHNICAL FIELD

The present invention relates to a magnetic field calibration device and, more particularly, to a magnetic field calibration device used to calibrate a magnetism measurement device having a plurality of magnetic sensors. The present invention also relates to a method of calibrating such a magnetism measurement device.

BACKGROUND ART

Recently, biomagnetism measuring devices such as a magnetoencephalograph, a magnetocardiograph and a magnetomyograph that detect weak biomagnetism generated from the heart, spinal cords, and peripheral nerves of a subject have been used for medical applications. Such biomagnetism measuring devices detect magnetism generated by a weak current accompanying the excitation of cells constituting these organs and are key devices for diagnosis of cardiac diseases, neurological disorders, and the like. The biomagnetism measuring devices generally use a SQUID sensor capable of detecting a weak magnetic field with high sensitivity.

In biomagnetism measurement using the SQUID sensor, a calibration operation is performed in advance so as to reduce measurement error. For example, Non-Patent Document 1 proposes a calibration method that performs magnetism measurement using the SQUID sensor while sequentially making current flow in a plurality of three-axis magnetic field coils disposed on a predetermined plane and uses the least square method to solve an inverse problem from a result of the measurement.

CITATION LIST

Non-Patent Document

[Non-Patent Document 1] Calibration for a Multichannel Magnetic Sensor Array of a Magnetospinography System, Yoshiaki Adachi et al. IEEE TRANSACTIONS ON MAGNETICS VOL. 50, NO. 11, NOVEMBER 2014.

SUMMARY OF THE INVENTION

Problem to be Solved by the Invention

However, the SQUID sensor needs to be cooled using liquid helium, increasing device scale and operation cost. Further, the SQUID sensor has only one measurement surface and has a structural difficulty in having two or more measurement surfaces.

Such problems may be solved by making a magnetic resistance sensor (hereinafter, abbreviated as "MR sensor") supersensitive in a magnetism measurement device having the MR sensors arranged in an array. The MR sensors include, for example, a giant magnetoresistance sensor (hereinafter, abbreviated as "GMR sensor"), a tunnel magnetoresistance sensor (hereinafter, abbreviated as "TMR sensor", and an anisotropic magnetoresistance sensor (hereinafter, abbreviated as "AMR sensor"). Such MR sensors are lower in price and smaller in size than the SQUID sensor and are thus widely used for non-contact rotation detection and position detection. Although there is no need to increase the sensitivity of the MR sensor in particular in the application range of the rotation detection and position detection, the supersensitive MR sensor is considered promising for an alternative to the SQUID sensor.

A biomagnetism measuring device using the MR sensor does not require cooling using liquid helium and can have two or more measurement surfaces while being miniaturized. Further, a fluxgate sensor and a magneto-impedance sensor, which operate at a room temperature, may be used as an alternative to the MR sensor.

However, with the calibration method described in the above Non-Patent Document 1, calibration needs to be performed for each measurement surface, so that when there are two or more measurement surfaces, calibration time is disadvantageously prolonged. In addition, calibration results are output separately for one measurement surface and another measurement surface, and thus the obtained results do not always match each other between the measurement surfaces.

It is therefore an object of the present invention to provide a magnetic field calibration device applied to calibration for a magnetism measurement device having two or more measurement surfaces and capable of reducing calibration time and allowing measurement results to match between measurement surfaces.

Means for Solving the Problem

A magnetic field calibration device according to the present invention is used to calibrate a magnetism measurement device having a plurality of magnetic sensors and includes a first holder having a first holding surface, a second holder having a second holding surface having a fixed relative positional relation with the first holding surface, at least one first magnetism generating part fixed to the first holding surface, and at least one second magnetism generating part fixed to the second holding surface.

A magnetism measurement device calibration method according to the present invention is a method of calibrating a magnetism measurement device having first and second measurement surfaces each provided with a plurality of magnetic sensors and generates magnetic fields from the first and second magnetism generating parts in a state where the magnetic field calibration device is fixed to the magnetism measurement device such that the first holding surface of the first holder faces the first measurement surface and that the second holding surface of the second holder faces the second measurement surface to calibrate the plurality of magnetic sensors.

According to the present invention, the magnetism generating part is provided on each of the first and second holding surfaces having a fixed relative positional relation, so that by assigning the first and second holding surfaces of the magnetic field calibration device respectively to the first and second measurement surfaces of the magnetism measurement device, calibration can be completed with a single operation. In addition, since the relative positional relation between the first and second holding surfaces is fixed, measurement results obtained from the individual measurement surfaces match each other.

In the present invention, the first and second magnetism generating parts may each include a first coil wound in a first axis direction, a second coil wound in a second axis direction perpendicular to the first axis direction, and a third coil wound in a third axis direction perpendicular to both the first axis direction and second axis direction. This allows magnetic fields to be generated in three directions from each of the first and second magnetism generating parts, thus allowing calibration to be performed more accurately.

In the present invention, a plurality of the first magnetism generating parts may be fixed to the first holding surface of the first holder, and a plurality of the second magnetism generating parts may be fixed to the second holding surface of the second holder. This allows a sufficiently strong reference magnetic signal to be given to both a magnetic sensor close to the first holding surface and away from the second holding surface and a magnetic sensor close to the second holding surface and away from the first holding surface, thus increasing the SN ratio of the measurement in the calibration operation. Thus, even when the magnetism measurement device has a plurality of measurement surfaces, calibration can be performed more accurately. Further, by accurately defining the relative distance and relative angle between the first and second holding parts, positioning accuracy of the relative positon between the magnetic sensors disposed in different measurement surfaces can be increased.

In this case, the plurality of first magnetism generating parts may be arranged in an array, and the plurality of second magnetism generating parts and some of the plurality of magnetism generating parts may be arranged in an array. With this configuration, some magnetism generating parts are assigned in common to two measurement surfaces provided in the magnetism measurement device, allowing the number of components to be reduced.

In the present invention, the first and second holding surfaces may be perpendicular to each other. This allows calibration to be performed for a magnetic measurement device having two measurement surfaces perpendicular to each other.

Advantageous Effects of the Invention

As described above, according to the present invention, there can be provided a magnetic field calibration device suitable for calibrating a magnetism measurement device having two or more measurement surfaces.

MODE FOR CARRYING OUT THE INVENTION

Preferred embodiments of the present invention will be explained below in detail with reference to the accompanying drawings.

Figure 1:
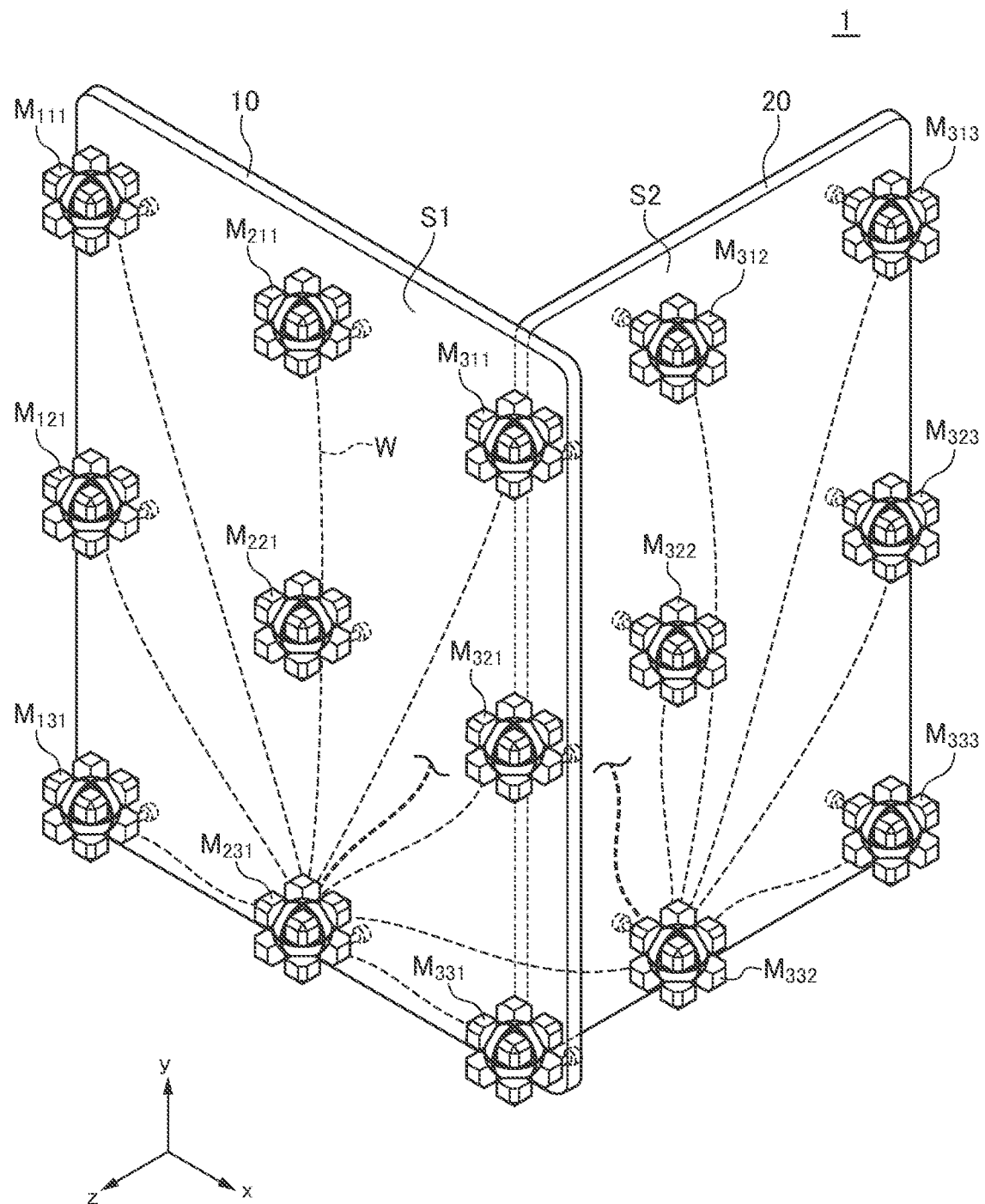
FIG. 1 is a schematic perspective view illustrating the outer appearance of a magnetic field calibration device 1 according to a preferred embodiment of the present invention.
Figure 2:
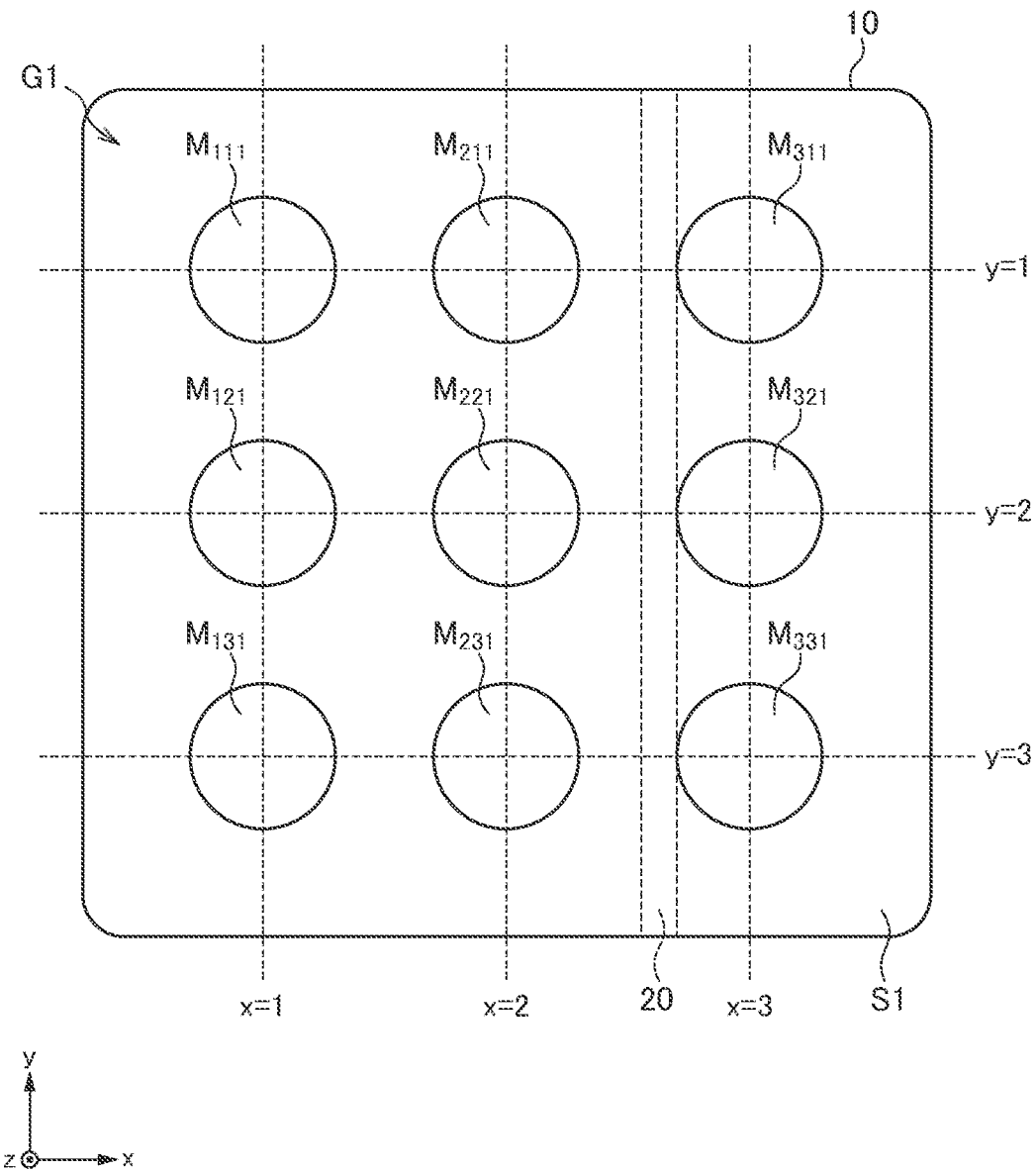
FIG. 2 is an xy plan view of the magnetic field calibration device 1 as viewed in the z-direction.

FIG. 1 is a schematic perspective view illustrating the outer appearance of a magnetic field calibration device 1 according to a preferred embodiment of the present invention. FIG. 2 is an xy plan view of the magnetic field calibration device 1 as viewed in the z-direction, and FIG. 3 is a yz plan view of the magnetic field calibration device 1 as viewed in the x-direction.

Figure 3:
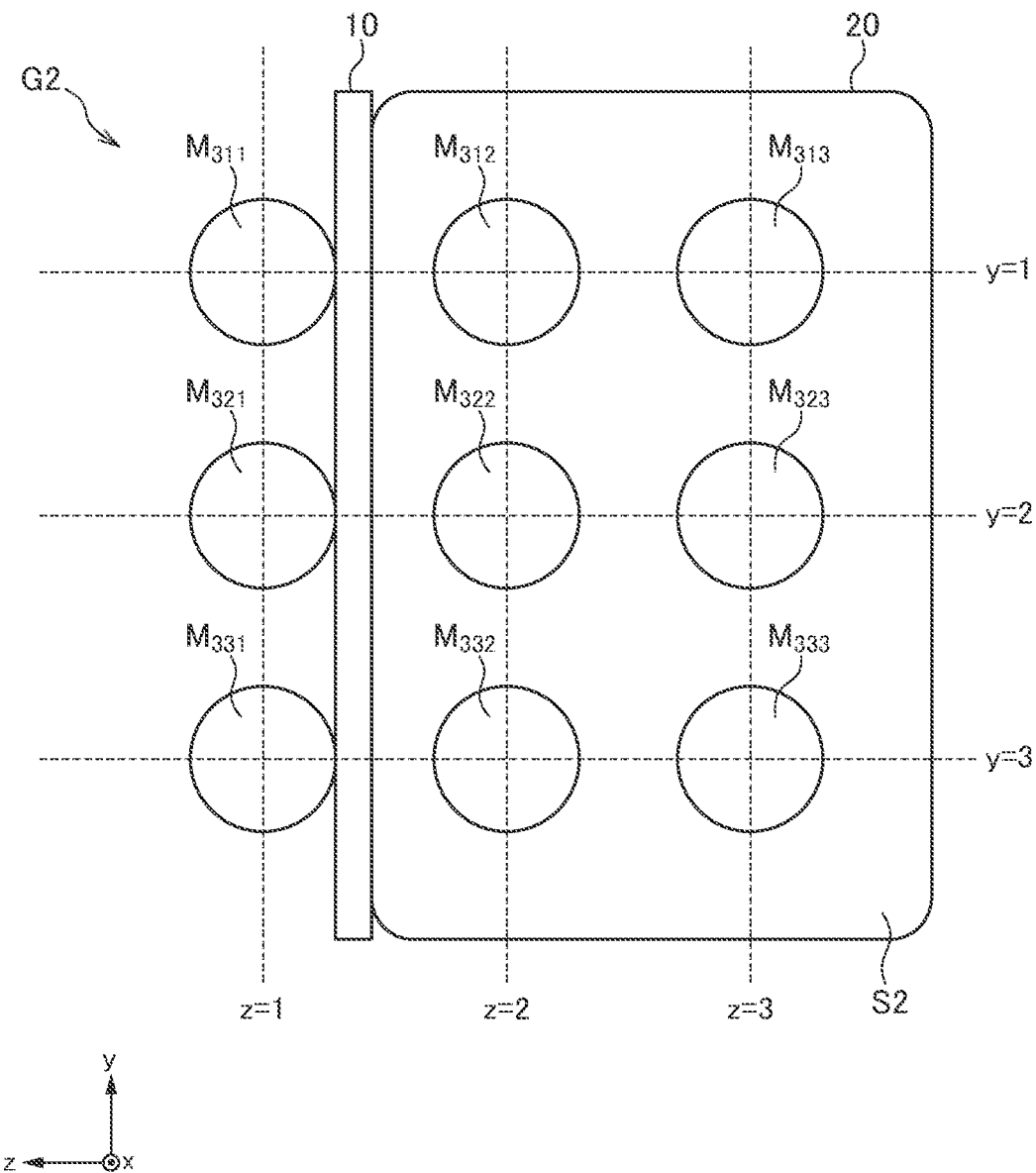
FIG. 3 is a yz plan view of the magnetic field calibration device 1 as viewed in the x-direction.

The magnetic field calibration device 1 according to the present embodiment is used in calibration for a magnetism measurement device and has, as illustrated in FIGS. 1 to 3, a first holder 10, a second holder 20, and a plurality of magnetism generating parts M fixed to a first holding surface S1 of the first holder 10 and a second holding surface S2 of the second holder 20. The first and second holders 10 and 20 each have a plate-like shape made of a nonmagnetic material such as acrylic and are fixed to each other. The first holding surface S1 of the first holder 10 constitutes the xy plane, and the second holding surface S2 of the second holder 20 constitutes the yz plane.

The first holding surface S1 of the first holder 10 has nine magnetism generating parts $M_{111}$, $M_{121}$, $M_{131}$, $M_{211}$, $M_{221}$, $M_{231}$, $M_{311}$, $M_{321}$, and $M_{331}$ fixed thereto. The second holding surface S2 of the second holder 20 has six magnetism generating parts $M_{312}$, $M_{322}$, $M_{332}$, $M_{313}$, $M_{323}$, and $M_{333}$ fixed thereto. The subscript xyz added to each magnetism generating part M indicates x-, y-, and z-coordinate positions. In the present specification, when there is no particular need to make a distinction between the plurality of magnetism generating parts M, they are collectively referred to as "magnetic generating part M" or "magnetic generating parts M".

As illustrated in FIG. 2, the nine magnetism generating parts $M_{111}$, $M_{121}$, $M_{131}$, $M_{211}$, $M_{221}$, $M_{231}$, $M_{311}$, $M_{321}$, and $M_{331}$ fixed to the first holding surface S1 constitute a first group G1 arranged in an array on the xy plane. The nine magnetism generating parts M constituting the first group G1 are the same in z-coordinate and different at least in one of x- and y-coordinates from one another. As illustrated in FIG. 3, the three magnetism generating parts $M_{311}$, $M_{321}$, and $M_{331}$ fixed to the first holding surface S1 and six magnetism generating parts $M_{312}$, $M_{322}$, $M_{332}$, $M_{313}$, $M_{323}$, and $M_{333}$ fixed to the second holding surface S2 constitute a second group G2. The nine magnetism generating parts M constituting the second group G2 are the same in x-coordinate and different at least in one of y- and z-coordinates from one another. Thus, the three magnetism generating parts $M_{311}$, $M_{321}$, and $M_{331}$ fixed to the first holding surface S1 belong to both the first and second groups G1 and G2.

Figure 4:
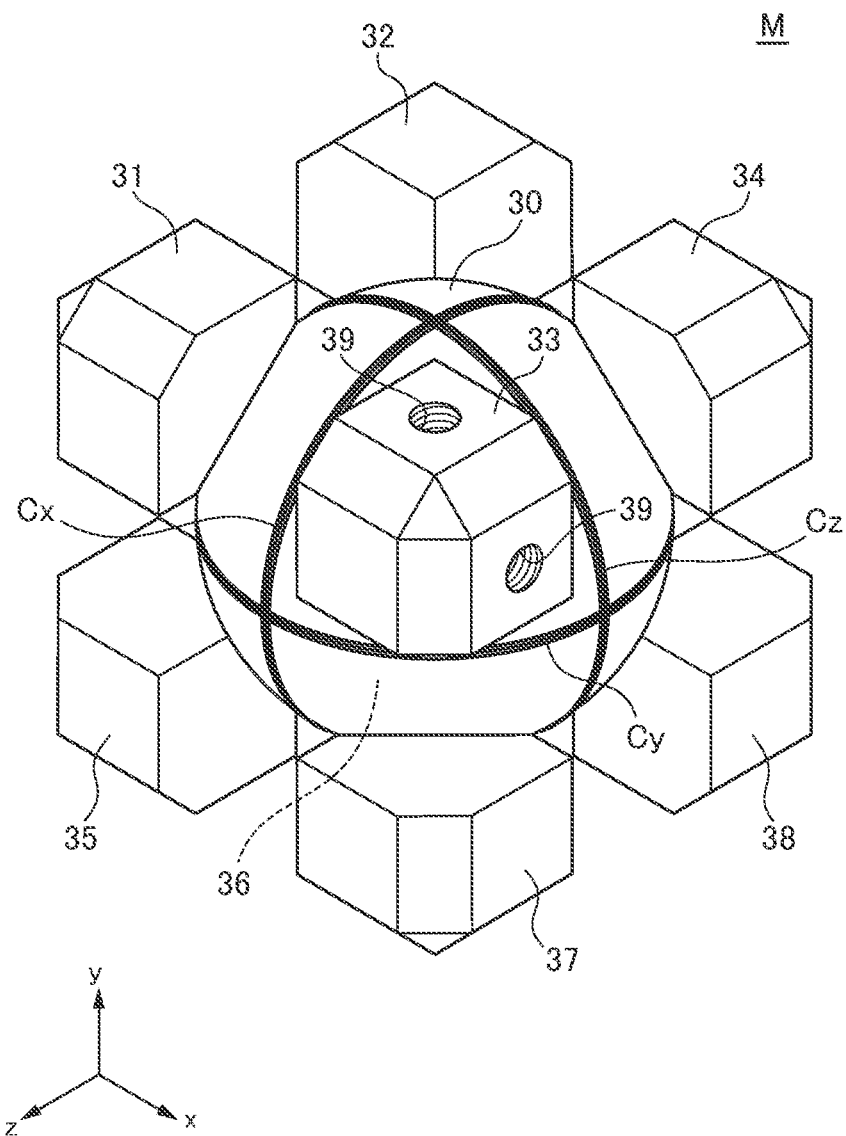
FIG. 4 is a schematic perspective view for explaining the structure of the magnetism generating part M.

FIG. 4 is a schematic perspective view for explaining the structure of the magnetism generating part M.

As illustrated in FIG. 4, the magnetism generating part M has a spherical bobbin 30, first, second, and third coils Cx, Cy, and Cz wound around the bobbin 30, and eight leg parts 31 to 38 connected to the bobbin 30. The first coil Cx is wound with the coil axis thereof directed along the x-axis direction, the second coil Cy is wound with the coil axis thereof directed along the y-axis direction, and the third coil Cz is wound with the coil axis thereof directed along the z-axis direction. The first, second, and third coils Cx, Cy, and Cz are independent of one another and can generate desired magnetic fields in the three-axis directions when applied with a current. Some of the leg parts 31 to 38 have screw holes 39 for fixing the magnetism generating part M to the first holder 10 or second holder 20.

Figure 5:
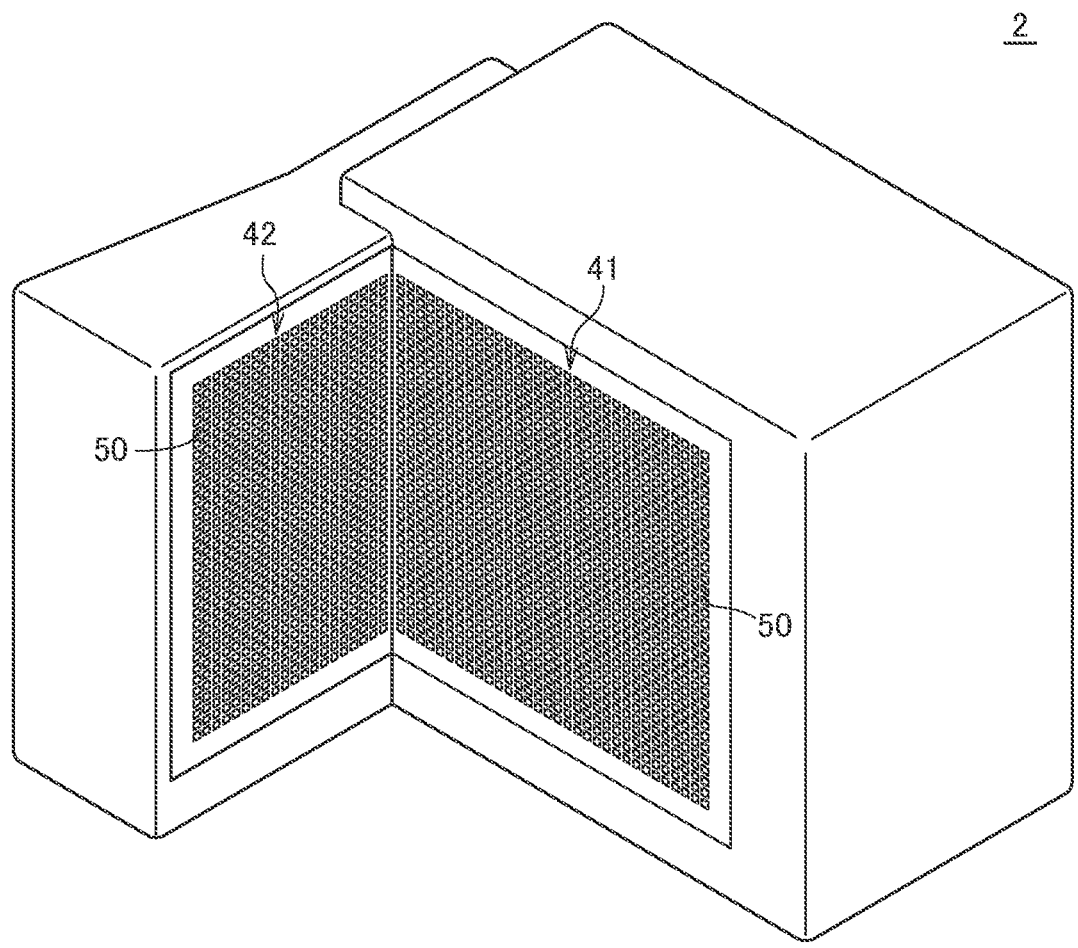
FIG. 5 is a schematic perspective view illustrating the outer appearance of a magnetism measurement device 2 which is subjected to calibration by the magnetic field calibration device 1.

FIG. 5 is a schematic perspective view illustrating the outer appearance of a magnetism measurement device 2 which is subjected to calibration by the magnetic field calibration device 1.

The magnetism measurement device 2 illustrated in FIG. 5 has a first measurement surface 41 constituting the xy plane and a second measurement surface 42 constituting the yz plane. On each of the first and second measurement surfaces 41 and 42, sensor heads of a plurality of magnetic sensors 50 are arranged in an array. Upon actual use of the magnetism measurement device 2, an object to be measured, e.g., a subject is placed in an area facing the first and second measurement surfaces 41 and 42, and a magnetic field is measured using the plurality of magnetic sensors 50 arranged in an array on the first measurement surface 41 and the plurality of magnetic sensors 50 arranged in an array on the second measurement surface 42. The magnetic sensor 50 has one or two or more magneto-sensitive elements which are MR sensors, for example. As the MR sensor, for example, a GMR sensor, a TMR sensor, and an AMR sensor may be used. Further, a fluxgate sensor and a magneto-impedance sensor may be used as an alternative to the MR sensor.

On the first measurement surface 41 of the magnetism measurement device 2, the sensor heads of the magnetic sensors 50 are arranged in an array in the xy-direction; on the second measurement surface 42 of the magnetism measurement device 2, the sensor heads of the magnetic sensors 50 are arranged in an array in the yz-direction. The use of the thus configured two measurement surfaces 41 and 42 allows a weak magnetic field generated from the object to be measured.

Although the position, inclination, and sensitivity of each magnetic sensor 50 are known to some degree at the manufacturing stage, the actual position, inclination, and sensitivity may include variations. Thus, when the magnetic field generated from the object to be measured is very weak, the variations result in large measurement error. Therefore, upon actual use of the magnetism measurement device 2, a calibration operation needs to be performed in advance. The magnetic field calibration device 1 according to the present embodiment is used for such a purpose.

Figure 6:
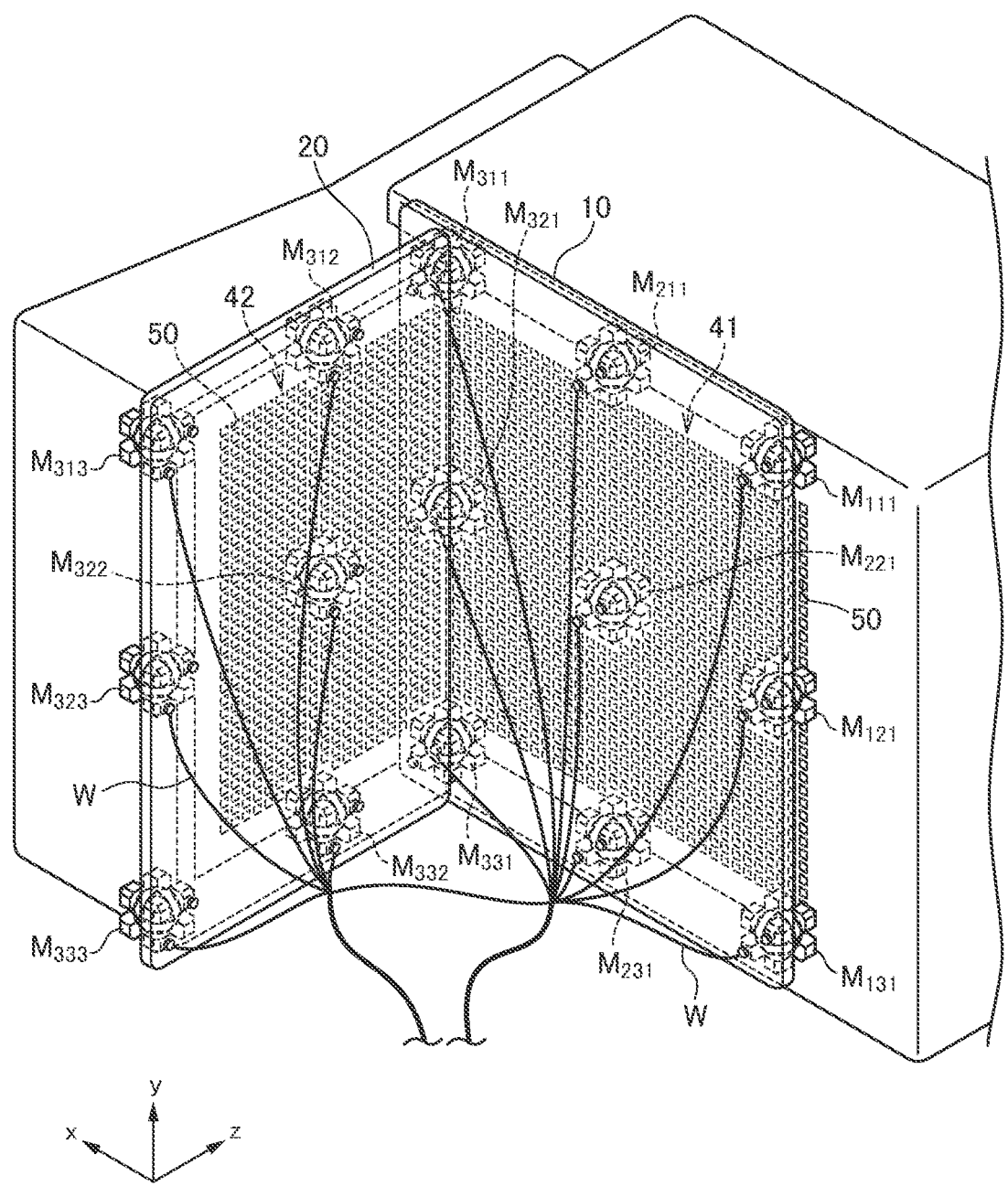
FIG. 6 is a schematic perspective view illustrating a state where the magnetic field calibration device 1 is used to calibrate the magnetism measurement device 2.

FIG. 6 is a schematic perspective view illustrating a state where the magnetic field calibration device 1 is used to calibrate the magnetism measurement device 2.

As illustrated in FIG. 6, when calibration is performed, the magnetic field calibration device 1 is fixed to the magnetism measurement device 2 such that the first holding surface S1 of the first holder 10 faces the first measurement surface 41 of the magnetism measurement device 2 and that the second holding surface S2 of the second holder 20 faces the second measurement surface 42 of the magnetism measurement device 2. The magnetic field calibration device 1 need not strictly be positioned with respect to the magnetism measurement device 2 and may be fixed to any position as long as the relative positional relation between the magnetic field calibration device 1 and the magnetism measurement device 2 does not change during calibration.

Thus, magnetic fields generated from the nine magnetism generating parts $M_{111}$, $M_{121}$, $M_{131}$, $M_{211}$, $M_{221}$, $M_{231}$, $M_{311}$, $M_{321}$, and $M_{331}$ constituting the first group G1 are mainly detected by the plurality of magnetic sensors 50 arranged on the first measurement surface 41, and magnetic fields generated from the nine magnetism generating parts $M_{311}$, $M_{321}$, $M_{331}$, $M_{312}$, $M_{322}$, $M_{332}$, $M_{313}$, $M_{323}$, and $M_{333}$ constituting the second group G2 are mainly detected by the plurality of magnetic sensors 50 arranged on the second measurement surface 42.

In calibration, current is made to flow individually in the coils Cx, Cy, and Cz included in each magnetism generating part M, magnetic fields generated at this time are measured by the magnetic sensors 50, whereby magnetic field data is acquired. The above operation is performed for each of the coils Cx, Cy, and Cz included in each magnetism generating part M, and the least square method is used to solve an inverse problem based on the acquired magnetic field data, whereby calibration for each magnetic sensor 50 is achieved.

Specifically, assuming that the output of the magnetic sensor 50 is $V_{meas}$ and that a magnetic field generated at the position of the magnetic sensor by each coil is $B_{meas}$, $B_{meas}=g \cdot V_{meas}$ is satisfied, where g is the sensitivity of the magnetic sensor 50. The position, inclination, and sensitivity of each magnetic sensor 50 is known to some degree, so that an estimated magnetic field $B_{cal}$ that will be given from each coil to each magnetic sensor 50 can be calculated by circle integration based on the position (x, y, z) from each coil, inclination (θ, φ), and sensitivity (G). The inclination θ indicates an angle in the z-direction about the x-axis, and the inclination φ indicates an angle in the y-direction about the x-axis. Then, by performing calculation using the least square method so as to minimize the value E in the following expressions (1), the actual position (x, y, z) and inclination (θ, φ) of the magnetic sensor 50 can be calculated.

[Numeral 1]

$$E = 1 - \frac{(B_{cal} \cdot V_{meas})^2}{|B_{cal}|^2 |V_{meas}|^2} \tag{1}$$

Further, by solving the following expression (2), the actual sensitivity g of the magnetic sensor 50 can be calculated.

[Numeral 2]

$$g = \frac{|B_{cal}|^2}{B_{cal} \cdot V_{meas}} \tag{2}$$

After the position, inclination, and sensitivity of each magnetic sensor 50 are thus acquired, the actual measurement values are corrected based on the obtained values, whereby accurate magnetism measurement can be performed.

As described above, the magnetic field calibration device 1 according to the present embodiment has a structure in which the first holder 10 having the first holding surface S1 constituting the xy plane and the second holder 20 having the second holding surface S2 constituting the yz plane are fixed to each other, and the first and second holding surfaces S1 and S2 each have the plurality of magnetism generating parts M, thereby allowing a calibration operation to be performed at a time for the magnetism measurement device 2 having the first measurement surface 41 constituting the xy plane and the second measurement surface 42 constituting the yz plane. In addition, the first and second holders 10 and 20 are fixed to each other, so that the measurement result obtained by the first measurement surface 41 and that obtained by the second measurement surface 42 match each other, that is, no error occurs between them.

Further, in the magnetic field calibration device 1 according to the present embodiment, the three magnetism generating parts $M_{311}$, $M_{321}$, and $M_{331}$ fixed to the first holding surface S1 belong to both the first and second groups G1 and G2, allowing the number of components to be reduced.

At least six coils are required in order to determine the six parameters of the position (x, y, z), inclination (θ, φ), and sensitivity (G). Thus, as long as the magnetism generating part M has the three coils Cx, Cy, and Cz, and magnetic fields generated from the coils can be detected by each magnetic sensor 50, it is possible to determine the above six parameters by providing at least one magnetism generating part M on each of the first and second holding surfaces S1 and S2.

Figure 7:
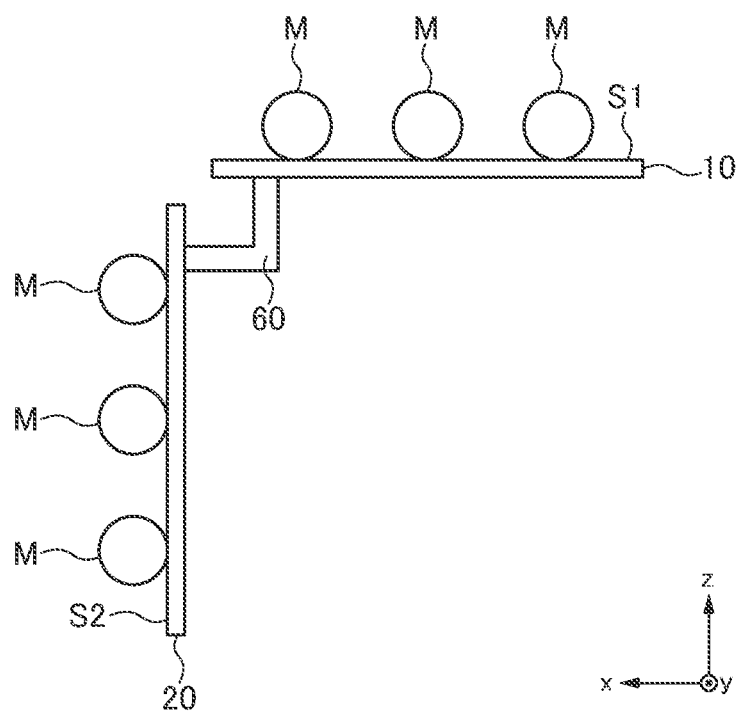
FIG. 7 is a schematic diagram illustrating a first modification.

Although the first and second holders 10 and 20 are directly fixed to each other in the above embodiment, they may be indirectly fixed to each other through a connecting member 60 as in a first modification illustrated in FIG. 7.

Figure 8:
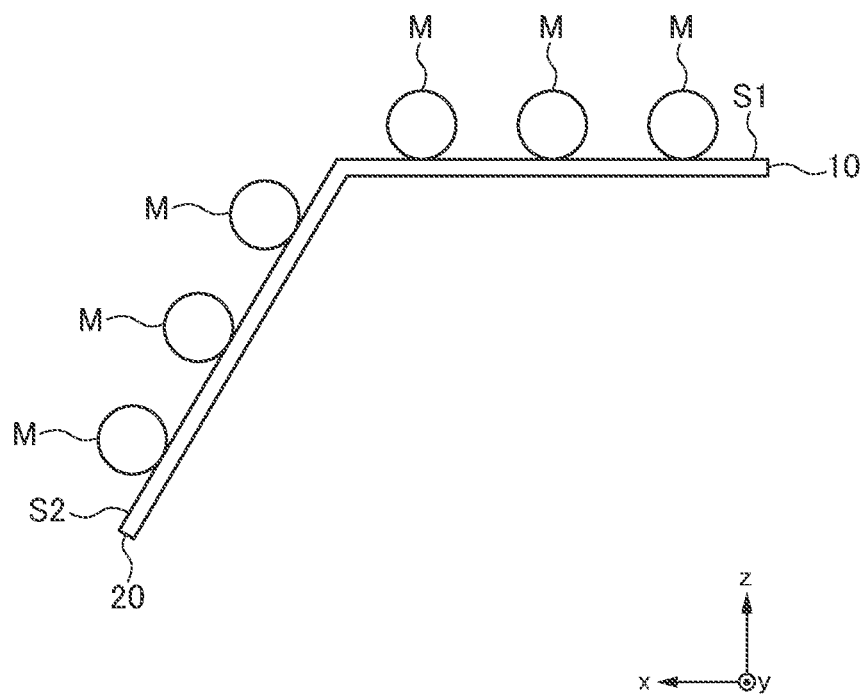
FIG. 8 is a schematic diagram illustrating a second modification.
Figure 9:
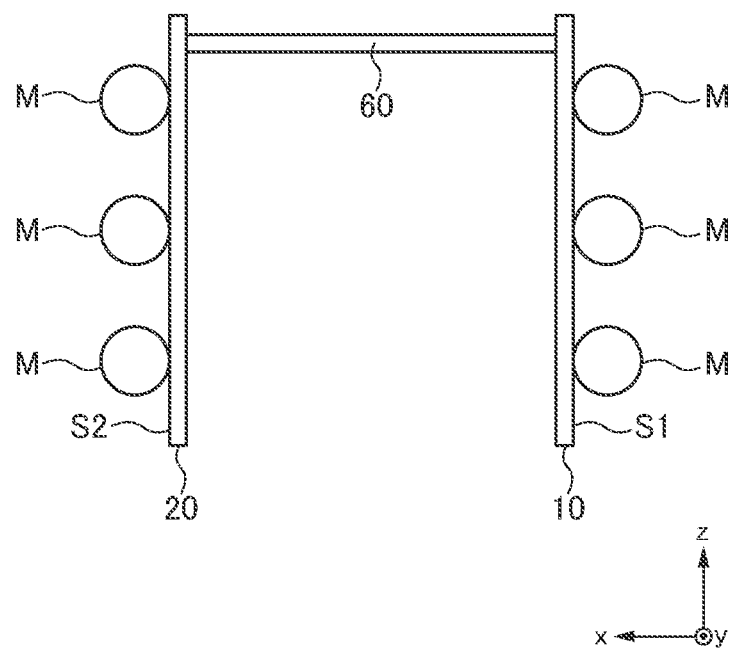
FIG. 9 is a schematic diagram illustrating a third modification.

Further, although the first holding surface S1 of the first holder 10 and the second holding surface S2 of the second holder 20 are perpendicular to each other in the above embodiment, they need not be perpendicular as in a second embodiment illustrated in FIG. 8. Although the angle formed by the first holding surface S1 and second holding surface S2 is obtuse in the example of FIG. 8, it may be acute. Further, the first and second holding surfaces S1 and S2 may be parallel to each other as in a third modification illustrated in FIG. 9. In the example of FIG. 9, both the first and second holding surfaces S1 and S2 constitute the yz plane.

Figure 10:
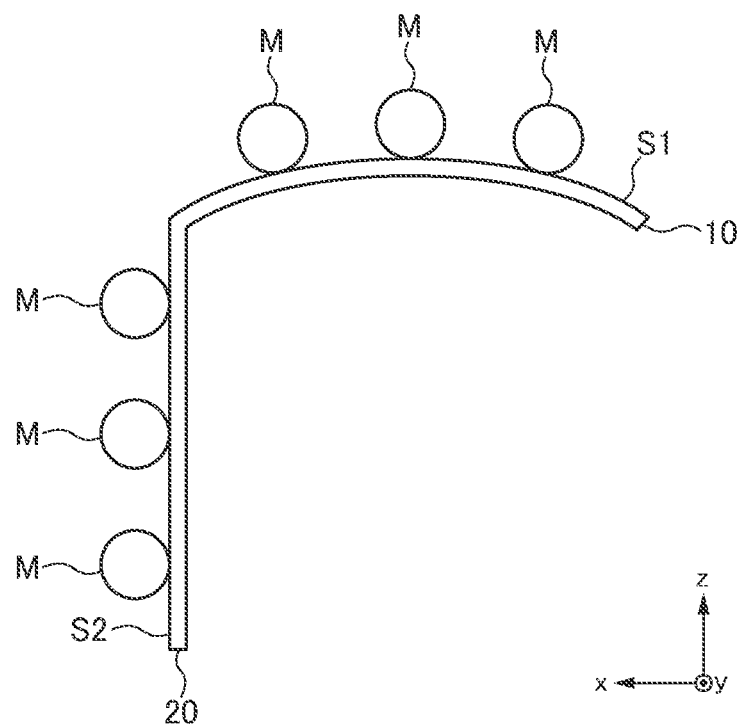
FIG. 10 is a schematic diagram illustrating a fourth modification.
Figure 11:
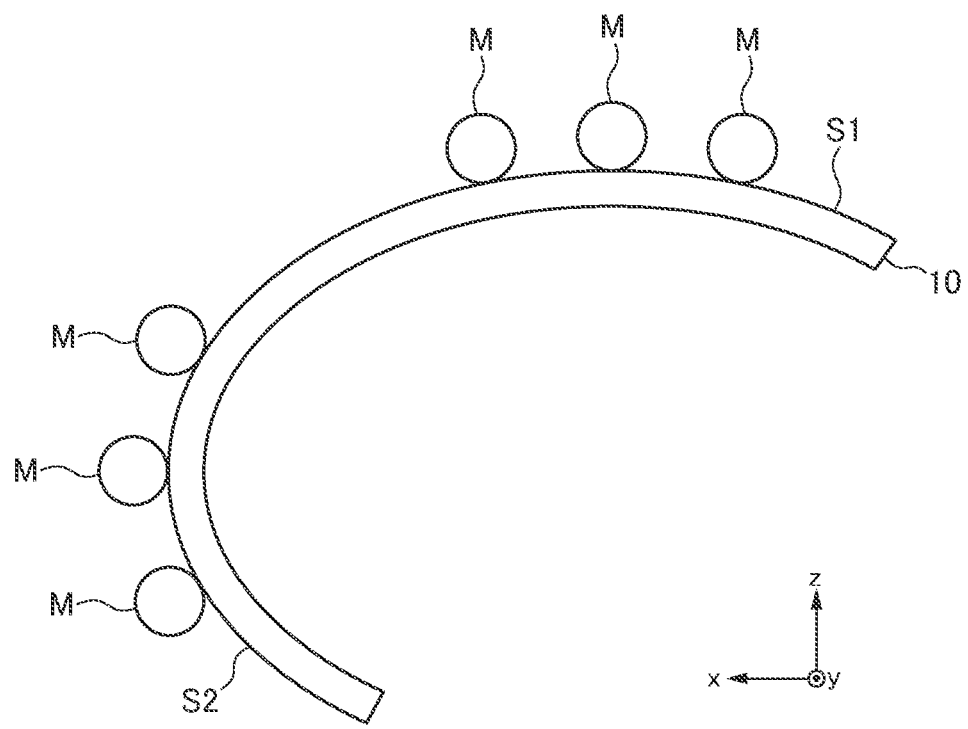
FIG. 11 is a schematic diagram illustrating a fifth modification.

Further, although both the first and second holding surfaces S1 and S2 are formed into a flat surface in the above embodiment, one or both of the first and second holding surfaces S1 and S2 may be formed into a curved surface as in a fourth modification illustrated in FIG. 10. In the example of FIG. 10, the first holding surface S1 is formed into a curved surface, and the second holding surface S2 is formed into a flat surface. Further, as in a fifth modification illustrated in FIG. 11, the first holder 10 may have both the first and second holding surfaces S1 and S2 which are formed in a continuous manner.

Figure 12:
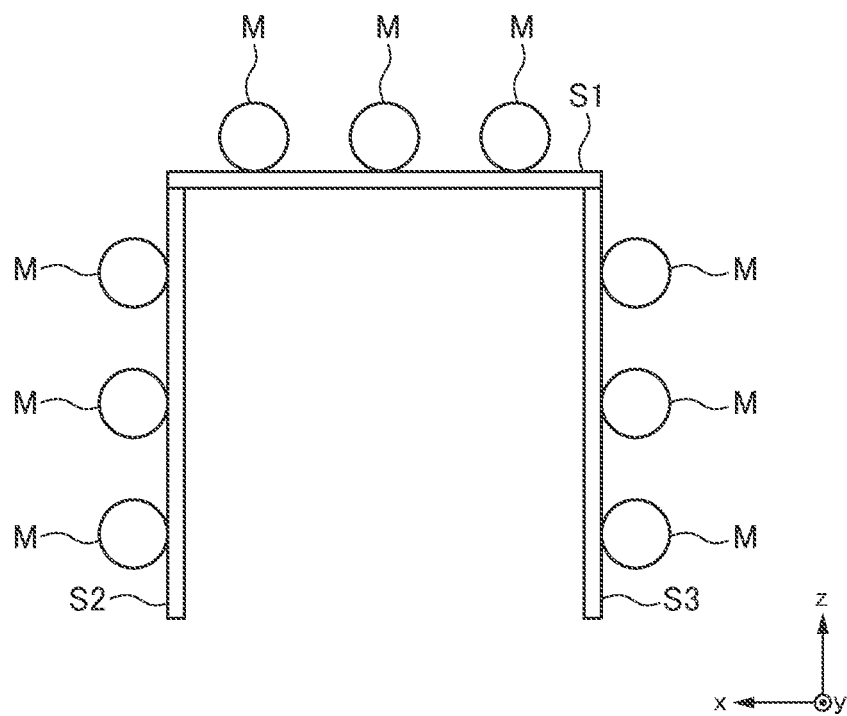
FIG. 12 is a schematic diagram illustrating a sixth modification.
Figure 13:
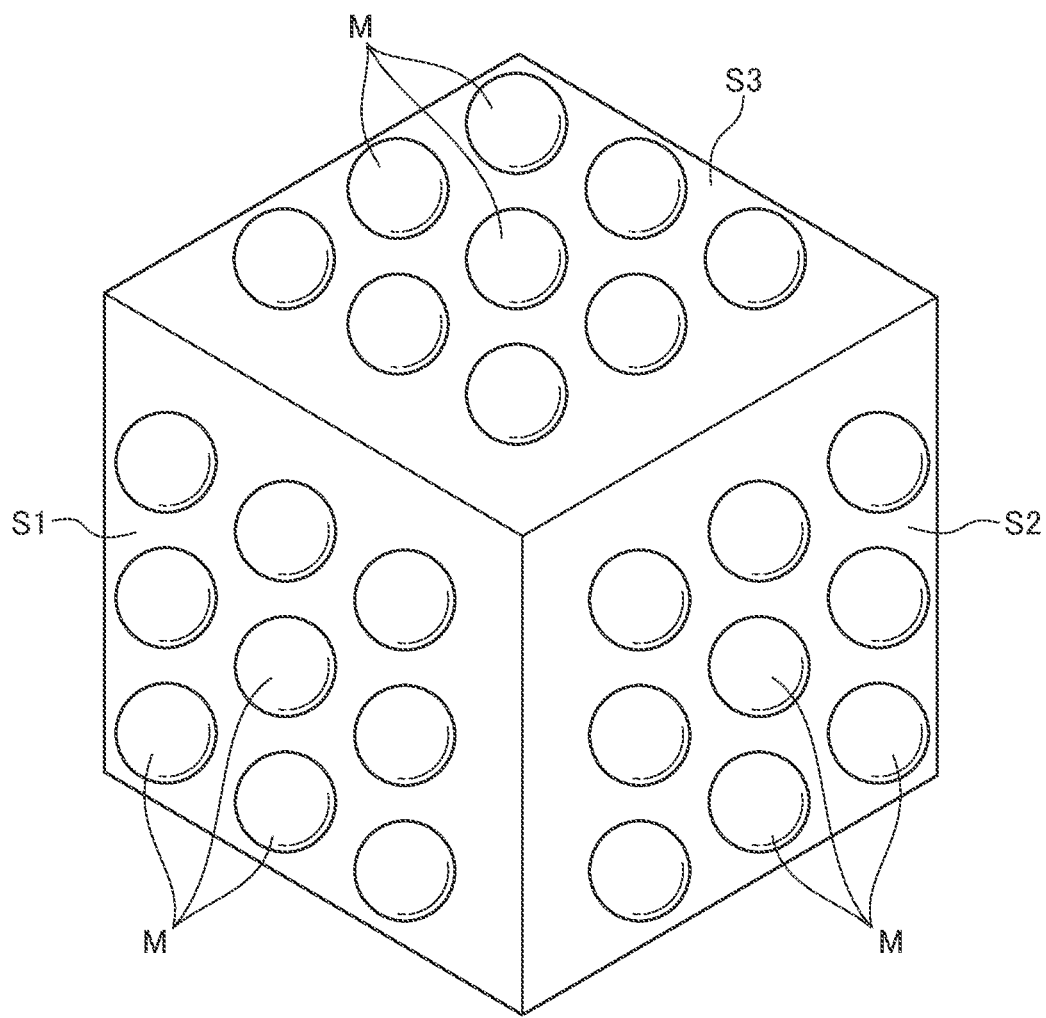
FIG. 13 is a schematic diagram illustrating a seventh modification.

Further, although the magnetism generating parts M are provided on the first and second holding surfaces S1 and S2 in the above embodiment, while the magnetic generating parts M may be provided on three surfaces as in a sixth modification illustrated in FIG. 12. In the example of FIG. 12, the first holding surface S1 constitutes the xy plane, and the second and third holding surfaces S2 and S3 constitute the yz plane. Further, as in a seventh modification illustrated in FIG. 13, the first holding surface S1, the second holding surface S2, and the third holding surface S3 may constitute the xy plane, yz plane, and xz plane, respectively. Further, although not illustrated, the magnetic field calibration device may have four or more surfaces to each of which the magnetism generating parts M are fixed.

It is apparent that the present invention is not limited to the above embodiments, but may be modified and changed without departing from the scope and spirit of the invention.

REFERENCE SIGNS LIST 1 magnetic field calibration device
2 magnetism measurement device
10 first holder
30 second holder
31-38 leg part
39 screw hole
41, 42 measurement surface
50 magnetic sensor
60 connecting member
Cx, Cy, Cz coil
G1 first group
G2 second group
M magnetism generating part
S1 first holding surface
S2 second holding surface
S3 third holding surface

What is claimed is:

1. A magnetic field calibration device used to calibrate a magnetism measurement device having a plurality of magnetic sensors, the magnetic field calibration device comprising:
   a first holder having a first holding surface;
   a second holder having a second holding surface having a fixed relative positional relation with the first holding surface;
   at least one first magnetism generating part fixed to the first holding surface; and
   at least one second magnetism generating part fixed to the second holding surface
   wherein each of the first and second magnetism generating parts includes a first coil wound in a first axis direction, a second coil wound in a second axis direction perpendicular to the first axis direction, and a third coil wound in a third axis direction perpendicular to both the first axis direction and second axis direction.

2. The magnetic field calibration device as claimed in claim 1, wherein a plurality of the first magnetism generating parts are fixed to the first holding surface of the first holder, and a plurality of the second magnetism generating parts are fixed to the second holding surface of the second holder.

3. The magnetic field calibration device as claimed in claim 2,
   wherein the plurality of first magnetism generating parts are arranged in an array, and
   wherein the plurality of second magnetism generating parts and some of the plurality of magnetism generating parts are arranged in an array.

4. The magnetic field calibration device as claimed in claim 1, wherein the first and second holding surfaces are perpendicular to each other.

5. A calibration method of a magnetism measurement device having first and second measurement surfaces each provided with a plurality of magnetic sensors, the calibration method comprising:

preparing a magnetic field calibration device comprising:
- a first holder having a first holding surface;
- a second holder having a second holding surface having a fixed relative positional relation with the first holding surface;
- at least one first magnetism generating part fixed to the first holding surface; and
- at least one second magnetism generating part fixed to the second holding surface; and generating magnetic fields from the first and second magnetism generating parts in a state where the magnetic field calibration device is fixed to the magnetism measurement device such that the first holding surface of the first holder faces the first measurement surface and that the second holding surface of the second holder faces the second measurement surface to calibrate the plurality of magnetic sensors.

6. A magnetic field calibration device used to calibrate a magnetism measurement device having a plurality of magnetic sensors, the magnetic field calibration device comprising:
- a first holder having a first holding surface;
- a second holder having a second holding surface that is not parallel with the first holding surface;
- a plurality of first coils fixed to the first holding surface; and
- a plurality of second coils fixed to the second holding surface.

7. The magnetic field calibration device as claimed in claim 6, wherein the plurality of first coils are arranged in an array on the first holding surface.

8. The magnetic field calibration device as claimed in claim 7, wherein the plurality of second coils are arranged in an array on the second holding surface.

9. The magnetic field calibration device as claimed in claim 6, wherein the first holding surface is substantially perpendicular to the second holding surface.

10. The magnetic field calibration device as claimed in claim 6, wherein a coil axis direction of one of the plurality of first coils is different from a coil axis direction of one of the plurality of second coils.

11. The magnetic field calibration device as claimed in claim 6, wherein a coil axis direction of one of the plurality of first coils is different from a coil axis direction of another one of the plurality of first coils.

12. The magnetic field calibration device as claimed in claim 11, wherein a coil axis direction of one of the plurality of second coils is different from a coil axis direction of another one of the plurality of second coils.

13. The magnetic field calibration device as claimed in claim 6, wherein a coil axis direction of one of the plurality of first coils and a coil axis direction of another one of the plurality of first coils are parallel with each other without coaxial.

14. The magnetic field calibration device as claimed in claim 13, wherein a coil axis direction of one of the plurality of second coils and a coil axis direction of another one of the plurality of second coils are parallel with each other without coaxial.

15. The magnetic field calibration device as claimed in claim 6, wherein a coil axis direction of one of the plurality of first coils and a coil axis direction of another one of the plurality of first coils are perpendicular to each other.

16. The magnetic field calibration device as claimed in claim 15, wherein a coil axis direction of one of the plurality of second coils and a coil axis direction of another one of the plurality of second coils are perpendicular to each other.

17. The magnetic field calibration device as claimed in claim 6, wherein each of the first and second holders has a plate-like shape.

18. The magnetic field calibration device as claimed in claim 6, wherein selected one of the plurality of first and second coils is supplied with current.

* * * * *